United States Patent [19]

Triplett et al.

[11] Patent Number: 5,922,587
[45] Date of Patent: Jul. 13, 1999

[54] PHOSPHOLIPID DEPENDENT PROTHROMBIN ACTIVATOR OBTAINED FROM SNAKE VENOM

[75] Inventors: Douglas A. Triplett, South Muncie, Ind.; Kurt Stocker, Aesch, Switzerland

[73] Assignee: Pentapharm AG, Basel, Switzerland

[21] Appl. No.: 08/472,005

[22] Filed: Jun. 6, 1995

Related U.S. Application Data

[62] Division of application No. 07/983,341, Nov. 30, 1992, Pat. No. 5,453,370.

[30]  Foreign Application Priority Data

Sep. 4, 1992 [EP]  European Pat. Off. .............. 92810679

[51] Int. Cl.$^6$ ................................. C12N 9/48; C12N 9/74
[52] U.S. Cl. ........................... 435/212; 435/214; 435/219
[58] Field of Search ..................................... 424/529, 542, 424/94.67; 435/212, 219; 530/856

[56]  References Cited

U.S. PATENT DOCUMENTS

| | | | |
|---|---|---|---|
| 4,106,992 | 8/1978 | Varirel et al. ......................... | 195/66 B |
| 4,725,673 | 2/1988 | Herring .................................. | 530/381 |
| 5,112,949 | 5/1992 | Vukovich ............................... | 530/380 |
| 5,192,689 | 3/1993 | Heinker et al. ......................... | 435/13 |
| 5,219,995 | 6/1993 | Herring et al. ......................... | 530/381 |
| 5,763,403 | 6/1998 | Lian ....................................... | 514/12 |

OTHER PUBLICATIONS

D.A. Triplett et al., "Lupus Anticoagulants: Misnomer, Paradox, Riddle Epiphenomenon," Hematol. pathol. 2, 121–143, 1988.

P.E. Love et al., "Antiphospholipid Antibodies: Anticardiolipin and the Lupus Anticoagulant in Systemic Lupus Erythematosus (SLE) and in Non–SLE Disorders," Ann. Int. Med. 112, 682–698, 1990.

T. Exner et al., SSC Subcommittee for the Standardization of Lupus Anticoagulants, "Guidelines for Testing and Revised Criteria for Lupus Anticoagulants," Thromb. Haemost. 65, 320–322, 1991.

J. Rosing et al., "Inventory of Exogenous Prothrombin Activators," Thrombosis and Haemostasis 65, 627–630, 1991.

P.P. Masci et al., "Purification and Characterization of a Prothrombin Activator from the Venom of the Australian Brown Snake, Pseudonaja textilis Textilis," Biochemistry International, 17, 825–835, 1988.

C.Y. Lee (ed.), Snake Venoms, pp. 15–40, Springer Verlag, Berlin, Heidelberg, New York (1979).

H. Hofmann et al., "Blood Coagulation Induced by the Venom of *Bothrops atrox* . 1. Identification, Purification, and Properties of a Prothrombin Activator," Biochemistry, 26, 772 (1987).

Journal of Biological Chemistry, vol. 261, No. 28, Oct. 5, 1986, pp. 13258–13267, H. Speijer et al. Prothrombin Activation By An Activator From The Venom Of *Oxyuranus Scutellatus* (Taipan Snake).

Thrombosis and Haemostasis, vol. 65, No. 3, Mar. 4, 1991, Stuttgart De, pp. 320–322, T. Exner et al., "Guidelines For Testing And Revised Criteria For Lupus Anticoagulants".

Thrombosis Research, vol. 3(6), 1973, pp. 705–714, G.G. Owen et al.

Thrombosis Research, vol. 1(6), 1972, pp. 559–568.

Govers–Rienslag, J.W.P. et al., "Haemostology", vol. 7, 1988, pp. 41–53, editor H. Pirkle et al., Marcel Dekko Inc., NY.

Thrombosis and Haemostasis, Speijer, H. et al., vol. 57(3), 1987 (Jun.), pp. 349–355.

Thrombosis and Haemostasis, vol. 42(1), Jul. 1979, p. 4000, #0954—abstract, Owen, W.G. et al.

Aust. N.Z.J. Med., vol. 18(3, s–pp1 #2), 1988, p. 430, abstract, Whitaker, An et al.

Scopes, R.K. Protein Purification—Principles and Procedure, 2nd edition, Springer–Verlag, 1987, p. 1, 17–20, 41–42, pp. 50–54.

Deutscher M.P. (ed.) Methods in Enzymology, vol. 182—Guide for protein Purification, Academic Process, Inc., 1990, p. 285, pp. 292–295.

Fohlman, J., "Toxican", vol. 17, 1979, pp. 170–172.

Tibbals, J., "Anaesth Intro Core", vol. 20(1), Feb. 1992, pp. 28–32.

Chester A. et al., Toxicon, vol. 20 (2), 1982, pp. 501–504.

Lalloo, O. et al., Toxicon, vol. 30(5–6), 1992, p. 528.

Masci, PP et al., Thrombosis Research, vol. 59, 1990, pp. 859–870.

Walker, F. J. et al. Biochemistry, vol. 19, 1980, pp. 1020–1023.

Nakagak, T. et al., Thrombosis Research, vol. 65, 1992, pp. 105–116.

T. Morita et al., "Purification and Properties of Prothrombin Activator from the Venom of *Echis carinatus*", J. Biochem. 83, 559–570 (1978).

(List continued on next page.)

*Primary Examiner*—Sandra E. Saucier
*Attorney, Agent, or Firm*—Pennie & Edmonds LLP

[57]  ABSTRACT

It was found that the use of a phospholipid dependent prothrombin activator purified from the venom of snakes belonging to the Elapidae family, especially members of the Oxyuranus and Psuedonaja genera is most useful in tests for the determination of Lupus Anticoagulant. Based on this, several clotting, chromogenic and immunochromogenic tests have been developed.

7 Claims, No Drawings

OTHER PUBLICATIONS

Cogger, H.G. (1992), Reptiles and Amphibians of Australia, 5th edition, pp. 660–663, 668–675, Reed International Books, Chatswood, Australia.

Goding, J.W. (1986), Monoclonal Antibodies: Principles and Practice, 2nd Edition, Academic Press, New York.

Krishnaswamy, S., Mann, K.G. and Nesheim, M.E. (1986), The Prothrombinase–catalyzed Activation of Prothrombin Proceeds Through the Intermediate Meizothrombin in an Ordered, Sequential Reaction, J. Biol. Chem. 201, No. 19, pp. 8977–8984.

Lottenberg, R., Christensen, U., Jackson, C.M. and Coleman, P.L. (1981), Assay of Coagulation Proteases Using Peptide Chromogenic and Flurogenic Substrates, Methods in Enzymology 80, pp. 341–361, Academic Press, New York.

Rosing, J. and Tans, G. (1992), Structural and Functional Properties of Snake Venom Prothrombin Activators, Toxicon, 30(12), pp. 1515–1527.

Stryer, L. (1988), Biochemistry (third edition), in particular p. 248, W.H. Freeman & Company, New York.

Triplett, D.A. and Brandt, J.T., Laboratory Identification of the Lupus Anticoagulant (1989) British Journal of Haematology, 73, pp. 139–142.

Triplett, D.A., Brandt, J.T., Musgrave, K.A. and Carol, A. (1988), The Relationship Between Lupus Anticoagulants and Antibodies to Phospholipid, JAMA 259, No. 4, pp. 550–556.

PHOSPHOLIPID DEPENDENT PROTHROMBIN ACTIVATOR OBTAINED FROM SNAKE VENOM

This is a division of application Ser. No. 07/983,341, filed Nov. 30, 1992, now U.S. Pat. No. 5,453,370.

FIELD OF THE INVENTION

The present invention relates to a phospholipid dependent prothrombin activator, to a method for its purification and to a test for the detection of Lupus Anticoagulant using the activator.

BACKGROUND OF THE INVENTION

The lupus anticoagulant (LA) is an immunoglobulin (IgG, IgM, or a mixture of both) which interferes with one or more of the in vitro phospholipid dependent tests of coagulation (activated partial thromboplastin time [APTT]; prothrombin time [PT]; dilute Russell Viper Venom Time [dRVVT]). In contrast to specific inhibitors of coagulation proteins, LA has no reactivity with any of the individual coagulation factors. The name is a misnomer since the vast majority of patients do not have underlying systemic lupus erythematosus (SLE). More commonly, LA is secondary to infections, drugs (e.g. chlorpromazine, quinidine, procainamide) or it may be seen in an autoimmune disease which has recently been described: Primary Antiphospholipid Antibody Syndrome.

Paradoxically, LA is not associated with clinical bleeding unless there is some associated hemostatic defect (e.g. thrombocytopenia). Approximately 30 to 40% of patients with LA have a history of venous and arterial thromboembolic events. For a number of years, there has been much discussion as to whether LA was causative, a consequence, or coincident with thrombosis. More recent work in animal models would suggest that indeed LA is a cause of a thrombotic predisposition. other clinical manifestations of LA include recurrent fetal loss, intra-uterine fetal growth retardation, and prematurity. Also, LA may be associated with thrombocytopenia or autoimmune hemolytic anemias. Two recent excellent reviews discuss LA and its closely related antibody: anticardiolipin antibodies [Triplett D. A., Brandt J. T., Lupus Anticoagulants: Misnomer, Paradox, Riddle Epiphenomenon. Hematol. Pathol. 2, 121–143, 1988; Love P. E., Santoro S. A., Antiphospholipid Antibodies: Anticardiolipin and the Lupus Anticoagulant in Systemic Lupus Erythematosus (SLE) and in Non-SLE Disorders. Ann. Int. Med. 112, 682–698, 1990].

In most cases, LA is detected serendipitous as a result of an unexplained prolonged APTT and/or PT. Typically, an abnormal APTT is associated with quantitative or qualitative deficiencies in factors XII, XI, IX, VIII, V, or X while PT prolongation generally indicates a deficiency in either factor II, V, VII, X, or fibrinogen. Mixing patient plasma with a source of normal platelet poor plasma will result in lack of correction of the prolonged APTT and/or PT. Lack of correction is a sine qua non for the diagnosis of an inhibitor (synonym circulating anticoagulant).

The diagnosis of LA is often difficult. Commercially available APTT reagents show a wide range of sensitivity to LA and there appears to be differences betwween IgG and IgM LA. In addition to the APTT, other tests have been used to screen for LA including: dilute Russell Viper Venom Time (dRVVT), Kaolin Clotting Time, and dilute APTT. The performance of these tests is difficult requiring mixing patient and normal plasma in the case of the Kaolin Clotting Time and dilute APTT. Consequently, these tests are not readily automated with conventional coagulation instrumentation. Furthermore, if commercial freeze-dried plasmas are used as a source of normal plasma for the mixing studies, there may be false negative results due to a high content of phospholipids in the lyophilized commercial preparations.

Once a patient plasma has been established as having a prolonged screening study with lack of correction by mixing with normal platelet poor plasma, it is necessary to confirm the phospholipid specificity of the inhibitor. Two contrasting approaches have been utilized. The first of these employs a dilute phospholipid test system (e.g. tissue thromboplastin inhibition [TTI]) to accentuate the inhibitor effect. The second approach utilizes a source of excess phospholipids (e.g. Platelet Neutralization Procedure [PNP]) to "bypass" or "neutralize" the LA. Comparative analysis of these two different approaches suggests the PNP is more sensitive than the TTI.

In addition to the heterogeneity of commercial available reagents, patient plasmas demonstrate remarkable heterogeneity suggesting that there is a family of antibodies with LA activity. The problems of diagnosing LA have been highlighted by the deliberations of the SSC Subcommittee for Standardization of Lupus Anticoagulants (Exner, T. et al., SSC Subcommittee for the Standardization of Lupus Anticoagulants, Guidelines for Testing and Revised Criteria for Lupus Anticoagulants. Thromb. Haemost. 65, 320–322, 1991).

The venoms of several snake species contain enzymes that convert the zymogen prothrombin into the enzyme thrombin and/or its catalytically active precursor meizothrombin. Both activation products convert fibrinogen into fibrin and thereby cause plasma coagulation. Also, both thrombin and meizothrombin catalyze the hydrolytic release of chromophore from synthetic chromogenic thrombin sensitive substrates. Some of these snake venom prothrombin activators do not require a cofactor while a second group depends on the presence of calcium ions and phospholipid. A third group needs factor V in addition to calcium and phospholipid. A review on snake venom prothrombin activators is presented by: Rosing J., Tans G., Thromb. Haemost. 65, 627–630, 1991.

Phospholipid dependent prothrombin activators whose potency is enhanced by phospholipid but not by factor V have been found in the venom of snakes belonging to the Elapidae family, especially members of the Oxyuranus and Psuedonaja genera. A method for the purification of the prothrombin activator from the venom of Psuedonaja textilis using chromatography on cancanavalin A-sepharose and gel filtration is described by Masci P. P. et al., Biochemistry International 17, 825, 1988. A commercial preparation of the activator prepared according to this method is available from Venom Supplies, Tanunda, Australia. The prothrombin activator isolated from P. textilis venom according to Masci et al. is a protein with a molecular mass of greater than 200,000 daltons consisting of several non-covalently linked subunits as shown by polyacrylamide gel electrophoresis in the presence of sodium dodecylsulfate (SDS-PAGE). The activator according to Masci et al. (1988) was able to clot citrated plasma in the absence of calcium ions. Its plasma clotting activity was, however, stimulated 2.5 fold in the presence of calcium but no additional stimulation was observed with the addition of phospholipids.

Prothrombin activators which are insensitive to phospholipids can be isolated from venoms of snakes belonging to the family Viperidae, especially from venoms of species belonging to the genera Echis, Trimeresurus, and Bothrops using conventional protein separation techniques as described by R. K. Scopes, Protein Purification, Springer-Verlag, New York, Heidelberg, Berlin, 2nd edition, (1987). A review on the zoological classification of venomous snakes can be found in G. Underwood, Classification and distribution of venomous snakes in the world. In: C. Y. Lee (ed). Snake Venoms p. 15–40, Springer Verlag: Berlin, Heidelberg, New York (1979). A specific method for the isolation of the prothrombin activator from *Bothrops atrox* venom is described by Hofmann H. and Bon C., Biochemistry 26, 772 (1987) and the method for the preparation of ECARIN (phospholipid independent prothrombin activator derived from *Echis carinatus* venom) is provided by Morita T. and Iwanaga S., J. Biochem. 83, 559 (1978). ECARIN activator is commercially available from Pentapharm Ltd., Basle, CH. One ECARIN activator unit is the amount of ECARIN activator which under defined conditions generates one International Unit (U) of enzyme activity from prothrombin as measured with the synthetic chromogenic thrombin substrate Tos-Gly-Pro-Arg-pNA (1 U being the amount of enzyme which hydrolyzes 1 $\mu$M of substrate per minute under standard conditions).

SUMMARY OF THE INVENTION

It was found that the clotting time of human citrated plasma following the addition of crude venom from the Australian brown snake *Pseudonaja textilis*, or of the commercially available prothrombin activator from this venom, was slightly shortened by the presence of phospholipid and calcium ions. It was also found that coagulation induced by *P. textilis* venom or by the commercial activator thereof (prepared according to Masci et al.), in the presence of phospholipid and calcium was not significantly delayed in LA containing plasma, as compared to normal plasma. It was then surprisingly found that the venom of *P. textilis* contained two different prothrombin activators, one of which required phospholipids and calcium ions for its action and was sensitive to LA, the second one acted independent from phospholipid and calcium and was insensitive to LA. It was moreover found that the phospholipid dependent prothrombin activator (PLDPA) from *P. textilis* venom was adsorbed to barium sulfate, while the phospholipid-independent prothrombin activator (PLIPA) remained in solution and that a simple purification process for the phospholipid-dependent activator could be based on this behaviour.

It was then found that PLDPA, purified by barium sulfate adsorption, exerted a very low plasma clotting activity in the absence of calcium and that the plasma clotting time measured following the addition of PLDPA in the presence of phospholipid and calcium was strongly prolonged by the presence of LA. It was in addition found that the clotting time, measured following the addition of the ECARIN activator was equal in both normal and LA containing plasma and it was finally found that both PLIPA and PLDPA clotting tests gave normal results with plasma depleted in factor V, VIII or X, respectively.

It is an object of the invention to provide a PLDPA from snake venom which can be used for the determination of LA.

It is another object of the invention to provide a method of purification of the snake venom.

It is still another object of the invention to provide different tests for the determination of LA and test kits which can be used for it.

DESCRIPTION OF THE PREFERRED EMBODIMENTS

PLDPA, free from contaminating PLIPA, is obtainable from aqueous solutions of the crude venom of *Pseudonaja textilis, P. affinis, P. nuchalis, Oxyuranus scutellatus* or *O. microlepidotus*, by 1.) adsorption to a practically water-insoluble barium salt e.g. barium sulfate, barium citrate, barium phosphate or by adsorption to aluminium hydroxide, magnesium hydroxide or tricalcium phosphate, 2.) washing the adsorbate with water or saline to remove non-adsorbed protein, 3.) elution of PLDPA with an aqueous solution of the alkali-, ammonium- or organic amine salt of acids which form practically insoluble salts, complexes or chelates with earth alkali- and aluminium ions e.g. citrate, morpholino ethane sulfonate, phosphate or ethylene diamine tetraacetate and 4.) removal of eluent by ultra-filtration, dialysis or gel filtration. The resulting PLDPA migrated by electrophoresis in the presence of SDS in a gel gradient of 8 to 25% polyacrylamide as one major band with a mobility corresponding to molecular mass of 40,000 to 60,000 Daltons and one or two minor bands with molecular mass between 100,000 and 150,000 Daltons. The plasma clotting activity measured on platelet poor human plasma of PLDPA according to the present invention was stimulated approximately 20 times by the addition of calcium ions and approx. 50 times by the addition of both calcium ions and phospholipid.

A clotting test, sensitive to LA can be carried out by mixing a plasma sample with a suitable amount of a phospholipid suspension and a solution of PLDPA, and by measuring the clotting time upon the addition of a sufficient amount of calcium chloride solution. The PLDPA clotting time is prolonged in LA containing plasma as compared to normal plasma; it is also prolonged in case of a quantitative or qualitative prothrombin abnormality, but it remains unaffected by deficiencies in factors V, VII, VIII, IX or X.

The clotting test can be simplified by the preparation of a reconstitutable reagent which contains PLDPA and phospholipid in a stable, co-lyophilized form. If desirable, the amount of calcium ions required for this test can also be co-lyophilized with PLDPA and phospholipid, if a non-hygroscopic calcium salt with a low freezing point depressor activity e.g. calcium gluconate or calcium lactobionate is used.

A chromogenic test for LA can be performed by mixing a plasma sample with PLDPA and phospholipid, adding calcium chloride, incubating this mixture for a defined activation time, quenching the prothrombin activation process by the addition of a chelating agent e.g. ethylene diamine tetraacetate containing buffer and measuring the generated amount of thrombin by means of a chromogenic substrate e.g. Tos-Gly-Pro-Arg-pNA. The amount of thrombin generated in LA containing plasma is significantly smaller as compared to the amount generated in normal plasma; it is also smaller in case of a qualitative or quantitative prothrombin abnormality.

A clotting test for LA, the result of which is not affected by a prothrombin deficiency, comprises the determination of the plasma clotting time after the addition of a PLIPA e.g. ECARIN, measurement of the clotting time after the addition of phospholipid and of a PLDPA, and calculation of the PLIPA/PLDPA clotting time ratio and/or the PLDPA/PLIPA clotting time ratio. Both PLIPA and PLDPA clotting times are inversed proportional to the prothrombin content of the plasma sample. However, while LA present in the sample, by interaction with the added phospholipids, causes a prolongation of PLDPA clotting time, the ECARIN activator clotting time remains unaffected. A PLIPA/PLDPA clotting time ratio below 1 or a PLDPA/PLIPA clotting time ratio above 1 (within reference interval) therefore indicates the presence of LA or of prothrombin with a molecular abnormality. The potency of PLIPA and PLDPA reagents according to the present invention is with preference adjusted in such a way that both reagents clot normal human plasma under defined conditions within the same time e.g. 20 seconds. The reagents for the PLIPA- and PLDPA test can be prepared in a liquid form with a limited stability, to be used within a limited time period or can be manufactured as stable, freeze dried preparations to be reconstituted with water or buffer to obtain the ready-for-use solution.

An immunochromogenic principle for an LA test can be carried out by coating a microtiter plate with phospholipid, adding a series of normal and patient plasma samples into the wells (to bind LA to the phospholipid layer), removal of plasma by rinsing, addition of a PLDPA and calcium-containing prothrombin solution to each well, quenching the activation by the addition of a chelating agent, adding a synthetic chromogenic thrombin substrate, quenching the reaction with acetic acid after a defined incubation period and measuring released chromophore by means of a microtiter plate reading photometer. This test principle is not affected by prothrombin abnormalities.

By the incorporation of prothrombin as the substrate for PLDPA in any of the above test methods, an interference by qualitative and/or quantitative prothrombin abnormalities can be avoided.

Phospholipids suitable for the performance of the PLDPA tests are preparations containing phosphatidylethanolamine (Synonym: colamine kephalin) and phosphatidylserine (Synonym: serine kephalin) which are obtainable from animal, plant or microbial biomass by organic solvent extraction. Suitable phospholipid preparations e.g. from bovine brain, egg yolk or soy bean are commercially available from Sigma Chemical Company, St. Louis, Mo., USA.

A stable, PLDPA reagent for reconstitution is obtainable by dissolving PLDPA purified according to the present invention and a protein-stabilizing polymer e.g. a collagen derived polypeptide and/or bovine serum albumin and/or dextran in water or buffer, adding a phospholipid suspension and freeze-drying this mixture after subdivision into vials suitable for reconstitution. If desirable, a lyophilizable calcium salt e.g. calcium gluconate or calcium lactobionate can be added.

A stable, PLIPA reagent for the PLIPA test according to the present invention is obtainable by dissolving ECARIN activator and a stabilizing polymer e.g. serum albumin and/or a collagen derived polypeptide and/or dextran in water or in a buffer solution and freeze-drying this solution subdivided into vials suitable for reconstitution.

The pH of the test reagents is adjusted to 7 to 8 preferentially to 7.4 and stabilized by means of a buffer system. Suitable buffer systems comprise for example tris (hydroxymethyl)-aminomethane hydrochloride (TRIS-HCl), 2-(N-morpholino)ethane-sulfonic acid (MES) and N-2-hydroxy-ethylpiperazine-N'-ethane-sulfonic acid (HEPES).

The PLIPA and PLDPA tests for LA in plasma can be carried out by measuring the time until onset of fibrin formation in the reaction mixture by manual or mechanical detection of gel formation or by photometric turbidity measurement.

EXAMPLE 1
Preparation of PLDPA from *P. textilis* Venom 50 mg crude *P. textilis* venom was dissolved in 100 ml aqueous tri-sodium citrate solution. 8 ml barium chloride solution, 1 M, were added, the mixture was stirred for 30 minutes, the formed precipitate was separated by centrifugation and dissolved in 33 ml of an aqueous solution of citrated saline (sodium chloride, 0.15 M and tri-sodium citrate 0.02 M). 2.64 ml of barium chloride, 1 M, were added to the solution and after 30 min. stirring, the formed precipitate was separated by centrifugation and the sediment was washed with 33 ml citrated saline. The washed sediment was dissolved in EDTA 0.2 M, pH 7.4, and EDTA-barium chelate was removed by ultrafiltration through a membrane with a cut-off of 10,000 Daltons and extensive washing with saline. The retentate was lyophilized to yield PLDPA which migrated in SDS-PAGE, using a gradient of 8 to 25% polyacrylamide, as one major band at a mobility corresponding to a molecular mass of 53,000 Daltons and two minor bands showing a molecular mass of 110,000 to 130,000 Daltons, respectively. A PLDPA solution adjusted to clot normal human citrated plasma in the presence of calcium chloride, 12.5 mM, and rabbit brain phospholipid, 17 $\mu$g/ml, within 20 seconds, showed a plasma clotting time in the absence of calcium ions and phospholipid of >900 seconds.

EXAMPLE 2
Preparation of a TEXTARIN Activator Reagent for Testing Phospholipid-dependent Prothrombin Activation Textarin prepared according to example 1 was dissolved in a solvent mixture consisting of 1% collagen-derived polypeptides (Prionex™, Pentapharm) in 0.05 molar HEPES buffer pH 7.4, to make 50 ml of stock solution I.

TEXTARIN is Pentapharm AG's trademark for the prothrombin activating component of *Pseudonaja textilis* snake venom used for the Lupus Anticoagulant test of the invention. It is referred to generically herein as "PLDPA". PRIONEX is a polypeptide fraction for the stabilization of proteins.

500 mg rabbit brain kephalin were homogenized in 5000 ml solvent mixture to obtain stock solution II.

Serial dilutions of stock solution I were prepared by mixing with stock solution II: The clotting time of citrated normal human plasma was then measured with each dilution using the following procedure: 0.1 ml dilution and 0.1 ml calcium chloride solution 0.025 M were incubated for 3 minutes at 37° C., 0.1 ml normal human plasma was then added and the clotting time was measured manually. A mixture of 1 volume stock solution I and 64 volumes stock solution II clotted normal plasma within 20 seconds. The total amount of PLDPA stock solution was diluted and mixed with kephalin accordingly, subdivided into 1.0 ml portions, filled into siliconized vials and freeze dried. The freeze-dried product, upon reconstitution with distilled water (1 ml per vial), gave a reagent which clotted citrated normal human plasma within 20±2 seconds in a test mixture composed of 0.1 ml plasma, 0.1 ml Textarin reagent and 0.1 ml $CaCl_2$.

EXAMPLE 3
Preparation of Ecarin Reagent for Testing Phospholipid-independent Prothrombin Activation 10 mg ECARIN activator with a potency of 500 EU per mg (ECARIN is a Pentapharm AG trademark for prothrombin activator derived from *Echis carinatus* venom) were dissolved in 50 ml of a solvent mixture consisting of 1% collagen-derived polypeptides (Prionex™, Pentapharm) in 0.05 molar HEPES buffer pH 7.4, to obtain ECARIN activator stock solution. Serial dilutions of stock solution with solvent mixture were prepared and the clotting time of citrated normal human plasma was measured manually at 37° C. using a test mixture of 0.2 ml plasma and 0.1 ml ECARIN activator dilution. The dilution which clotted normal plasma within 20 seconds was determined and the ECARIN activator stock solution was diluted accordingly to yield a solution with approx. 16 EU per ml, ready for freeze-drying. The solution was subdivided into portions of 1.0 ml, filled into suitable vials and freeze-dried. The freeze-dried product, after reconstitution with 1.0 ml distilled water, gave a reagent which clotted citrated normal human plasma in 20±2 seconds, in a test mixture composed of 0.2 ml plasma and 0.1 ml ECARIN activator reagent.

EXAMPLE 4
TEXTARIN Activator and ECARIN Activator Clotting Test for LA

TEXTARIN activator reagent according to example 2 and ECARIN activator reagent according to example 3 were reconstituted with 1.0 ml distilled water per vial.

TEXTARIN- activator and ECARIN activator clotting times of plasma samples collected from ten pre-operative patients with a normal blood coagulation status and of ten plasma samples containing LA, as verified immunologically, were determined. The results are listed in tables 1 and 2.

TABLE 1

ECARIN activator and TEXTARIN activator clotting times of plasma with a normal clotting status

| Plasma | ECARIN activator ct (sec.) | TEXTARIN activator ct (sec.) | TEXTARIN/ECARIN ratio |
|---|---|---|---|
| 1 | 17.3 | 21.2 | 1.23 |
| 2 | 18.7 | 18.0 | 0.96 |
| 3 | 20.2 | 19.5 | 0.97 |
| 4 | 17.1 | 18.1 | 1.06 |
| 5 | 17.1 | 17.9 | 1.05 |
| 6 | 17.0 | 17.6 | 1.04 |
| 7 | 17.4 | 18.6 | 1.07 |
| 8 | 14.6 | 17.9 | 1.23 |
| 9 | 15.8 | 17.4 | 1.10 |
| 10 | 20.6 | 17.5 | 0.85 |

TABLE 2

ECARIN activator and TEXTARIN activator clotting times of LA-containing plasma

| Plasma | ECARIN activator ct (sec.) | TEXTARIN activator ct (sec.) | Tex./Ec. ratio |
|---|---|---|---|
| 11 | 17.4 | 27.8 | 1.60 |
| 12 | 13.9 | 34.1 | 2.45 |
| 13 | 19.0 | 24.7 | 1.30 |
| 14 | 14.4 | 40.7 | 2.83 |
| 15 | 16.6 | 38.8 | 2.34 |
| 16 | 18.7 | 41.2 | 2.20 |
| 17 | 20.5 | 75.5 | 3.68 |
| 18 | 21.1 | 90.1 | 4.27 |
| 19 | 14.4 | 28.2 | 1.96 |
| 20 | 15.9 | 58.9 | 3.70 |
| 21 | 22.5 | 38.8 | 1.72 |
| 22 | 17.8 | 75.9 | 4.26 |

EXAMPLE 5
Chromogenic TEXTARIN Activator Test

Material: TEXTARIN activator reagent according to example 2 was reconstituted with 1 ml distilled water per vial. The chromogenic thrombin substrate Tos-Gly-Pro-Arg-pNA (Chromozym TH$^R$, a tripeptide for the determination of proteolytical enzymes manufactured by Pentapharm Ltd., distributed by Boehringer-Mannheim) was dissolved in distilled water at a concentration of 4 1 μmoles per ml. Calcium chloride/GPRP solution contained 0.025 mmoles $CaCl_2$ and 0.5 mg Gly-Pro-Arg-Pro (GPRP, Pefabloc FG$^R$, an inhibitor of fibrin polymerisation, Pentapharm) per ml. EDTA-buffer was glycine-NaOH buffer, 0.3 M, pH 8.4, 0.75 mM in EDTA.Na$_2$.

Test: 0.020 ml TEXTARIN activator reagent and 0.020 ml $CaCl_2$/GPRP were pipetted into a photometric cuvette and preheated for 2 minutes at 37° C., 0.020 ml plasma sample were added and incubated for exactly 30 seconds at 37° C. The activation process was quenched by the addition of 1.74 ml EDTA-buffer, 0.200 ml Chromozym TH$^R$ were added and the p-nitroaniline release catalyzed by generated thrombin was recorded with a photometer at a wave length of 405 nm. The difference in absorbance per minute (DA 405/min.) which is directly proportional to the generated amount of thrombin was measured in normal and LA containing plasma samples.

Results: DA 405/min. values of normal plasma varied between 0.07 and 0.1, whereas LA containing plasma samples gave values of 0.02 to 0.06.

EXAMPLE 6
Preparation of Phospholipid Dependent Prothrombin Activator (PLDPA) from Venom of Different Snake Species Samples of 5 mg each of dried, crude venom from *Oxyuranus scutellatus, O. microlepidotus, Pseudonaja textilis, P. inframaculata* and *P. nuchalis* were dissolved in 10 ml aqueous tri-sodium citrate solution. 0.8 ml barium chloride solution, 1 M, was added, the mixture was stirred for 30 minutes, the formed precipitate was separated by centrifugation and dissolved in 3 ml of an aqueous solution of citrated saline (sodium chloride, 0.15 M and tri-sodium citrate 0.02 M). 0.25 ml of barium chloride, 1 M, was added to the solution and after 30 min. stirring, the formed precipitate was separated by centrifugation and the sediment was dissolved in EDTA 0.2 M, pH 7.4 to obtain a stock solution for prothrombin activation tests.

Human plasma clotting time was measured with dilutions of each stock solution in the presence and absence of phospholipid and calcium ions. The results are presented in table 3.

TABLE 3

Clotting time of PLDPA from different snake venoms

| | | clotting time (sec) | |
|---|---|---|---|
| Species | dilution of stock soln. | Ca/PL present (double determination) | Ca/PL absent |
| *O. scutellatus* | 1/200 | 41.2/41.2 | 111.0/112.0 |
| *O. microlepidotus* | 1/200 | 34.0/34.0 | 151.0/151.0 |
| *P. textilis* | 1/1000 | 26.0/27.0 | 230.0/233.0 |
| *P. inframaculata* | 1/500 | 25.0/25.0 | 112.0/114.0 |
| *P. nuchalis* | 1/500 | 30.0/30.0 | 75.0/74.0 |

We claim:
1. A phospholipid dependent prothrombin activator suitable for the detection of Lupus Anticoagulant obtainable by chemical purification from the venom of *Pseudonaja textilis*, the activator being an enzyme identifiable from the following characteristics:
   a) in the presence of calcium ions and phospholipids the activator exhibits an increased plasma clotting activity which is:
      (i) reduced in the presence of Lupus Anticoagulant,
      (ii) unaffected by a deficiency in any one of clotting Factors V, VII, VIII, IX or X,
   b) the activator exhibits a major band at a mobility corresponding to a molecular mass of 40,000 to 60,000

Daltons in the presence of SDS in a gel gradient of 8 to 25% polyacrylamide and no bands are exhibited above 150,000 Daltons; and c) the activator is essentially free from contaminating phospholipid independent activator.

2. The activator according to claim 1, wherein the plasma clotting activity is stimulated by the addition of 12.5 mM calcium ions and 17 μg/ml rabbit brain phospholipids.

3. The activator according to claim 1, isolated and purified from the venom of *Pseudonaja affinis, Pseudonaja nuchalis, Pseudonaja textilis, Oxyuranus scutellatus,* or *Oxyuranus microlepidotus.*

4. The activator according to claim 1, isolated and purified from the venom of *Pseudonaja textilis.*

5. An enzyme obtained from the venom of snakes for converting prothrombin into thrombin identifiable from the following characteristics:

a) in the presence of 12.5 mM calcium ions and 17 μg/ml rabbit brain phospholipids, the enzyme exhibits clotting activity of platelet poor plasma which is:

(i) reduced in the presence of Lupus Anticoagulant, and (ii) unaffected by a deficiency in said plasma of any one of clotting Factors V, VII, VIII, IX or X, b) the enzyme exhibits a major band at a mobility corresponding to a molecular mass of 40,000 to 60,000 Daltons in the presence of SDS in a gel gradient of 8 to 25% polyacrylamide and no bands are exhibited above 150,000 Daltons; and c) the enzyme is essentially free from phospholipid independent prothrombin-converting enzyme.

6. The enzyme according to claim 5, isolated and purified from the venom of *Pseudonaja affinis, Pseudonaja nuchalis, Pseudonaja textilis, Oxyuranus scutellatus,* or *Oxyuranus microlepidotus.*

7. The enzyme according to claim 5, isolated and purified from the venom of *Pseudonaja textilis.*

\* \* \* \* \*